(12) United States Patent
Bhadra et al.

(10) Patent No.: US 11,000,459 B2
(45) Date of Patent: May 11, 2021

(54) SILICA ABRASIVES WITH HIGH STANNOUS FLUORIDE COMPATIBILITY

(71) Applicant: Colgate-Palmolive Company, New York, NY (US)

(72) Inventors: Madhuleena Bhadra, Metuchen, NJ (US); Michael Prencipe, West Windsor, NJ (US); Aarti Rege, East Windsor, NJ (US)

(73) Assignee: Colgate-Palmolive Company, New York, NY (US)

( * ) Notice: Subject to any disclaimer, the term of this patent is extended or adjusted under 35 U.S.C. 154(b) by 45 days.

(21) Appl. No.: 16/216,345

(22) Filed: Dec. 11, 2018

(65) Prior Publication Data

US 2019/0183748 A1 Jun. 20, 2019

Related U.S. Application Data

(60) Provisional application No. 62/599,383, filed on Dec. 15, 2017.

(51) Int. Cl.
| | | |
|---|---|---|
| *A61K 8/21* | (2006.01) | |
| *A61K 8/25* | (2006.01) | |
| *A61K 8/27* | (2006.01) | |
| *A61K 8/365* | (2006.01) | |
| *A61Q 11/00* | (2006.01) | |
| *C09K 3/14* | (2006.01) | |

(52) U.S. Cl.
CPC ............... *A61K 8/21* (2013.01); *A61K 8/25* (2013.01); *A61K 8/27* (2013.01); *A61K 8/365* (2013.01); *A61Q 11/00* (2013.01); *A61K 2800/28* (2013.01); *A61K 2800/412* (2013.01); *A61K 2800/5922* (2013.01); *C09K 3/1409* (2013.01)

(58) Field of Classification Search
None
See application file for complete search history.

(56) References Cited

U.S. PATENT DOCUMENTS

| | | | |
|---|---|---|---|
| 4,340,583 A | 7/1982 | Wason | |
| 5,658,553 A | 8/1997 | Rice | |
| 6,946,119 B2 | 9/2005 | Gallis et al. | |
| 8,216,553 B2 | 7/2012 | Hughes et al. | |
| 2009/0010973 A1* | 1/2009 | Stanier | A61Q 11/00 424/401 |
| 2012/0100193 A1 | 4/2012 | Nowak et al. | |

FOREIGN PATENT DOCUMENTS

| | | |
|---|---|---|
| WO | 2003/000217 | 1/2003 |
| WO | 2013/033090 | 3/2013 |
| WO | 2018/118382 | 6/2018 |

OTHER PUBLICATIONS

International Search Report and the Written Opinion of the International Searching Authority issued in international application PCT/US2018/064920 dated Feb. 18, 2019.

* cited by examiner

*Primary Examiner* — Nannette Holloman

(57) ABSTRACT

This invention relates to dentifrice compositions comprising stannous fluoride and a silica abrasive having a $N_2$ BET surface area of less than 50 $m^2$/g and an Einlehner hardness of from 4 to 11, as well as to methods of using these compositions.

14 Claims, No Drawings

SILICA ABRASIVES WITH HIGH STANNOUS FLUORIDE COMPATIBILITY

CROSS REFERENCE TO RELATED APPLICATIONS

This application claims the benefit and priority of U.S. provisional application 62/599,383, filed on Dec. 15, 2017.

BACKGROUND

Abrasives in oral compositions debride and physically scrub the external surface of the teeth. This scrubbing action removes organic biofilm (i.e., the pellicle) on the tooth surface that is formed primarily of salivary proteins, bacteria, and bacterial byproducts. Pellicle may also be stained and discolored by foods, such as coffee, tea and berries, as well as, by tobacco smoke, cationic compounds, and chromogenic bacteria. Such physical removal of the stained pellicle is a simple and effective means of removing the undesirable surface staining and discoloration which occurs daily. Further, such physical removal of the pellicle also removes plaque bacteria on the pellicle surface, thereby minimizing the potential for gingivitis, periodontitis, and caries formation. However, oral compositions such as dentifrices should not have such high abrasiveness that potential damage to the enamel or tissue may result. As such, it is desirable to develop oral compositions that optimize the cleaning and/or polishing efficacy of the oral composition, while minimizing the harmful abrasiveness to avoid potential damage oral surfaces.

Stannous fluoride is well known for use in clinical dentistry with a history of therapeutic benefits dating back to the early 1950s. Stannous fluoride has been reported to be an effective agent for treating various oral conditions and diseases including plaque, gingivitis, sensitivity, enamel decalcification, and periodontitis, among others. However, the production of an abrasive toothpaste containing stannous fluoride has presented compatibility problems. Although silica abrasives are widely used within toothpastes, the surface hydroxyl groups on the silica particles can interact with stannous ions. Such interaction has a negative effect on the stability of stannous ions over the shelf life of the toothpaste. Silica abrasives also tend to interact with fluoride ions and thus diminish the ability of the fluoride ion source to provide soluble fluoride upon use.

Accordingly, there exists a need for silica abrasives which exhibit high stannous fluoride compatibility as well as acceptable cleaning performance and low dental abrasion.

BRIEF SUMMARY

It has been found that silica abrasives having a $N_2$ BET surface area of less than 50 $m^2/g$ exhibit high stannous and fluoride ions compatibility. The invention provides dentifrice compositions comprising a stannous ion source, a fluoride ion source and a silica abrasive having a $N_2$ BET surface area of less than 50 $m^2/g$ and an Einlehner hardness of from 4 to 11. In some embodiments, the dentifrice compositions of the invention also have a high pellicle cleaning ratio (PCR), but a low degree of dental abrasion, which is measured as radioactive dental abrasion (RDA). Preferably, the stannous ion and fluoride ion source is stannous fluoride.

The invention further encompasses methods comprising applying an effective amount of a dentifrice as disclosed herein to the oral cavity, e.g., by brushing, to a subject in need thereof, to (i) reduce or inhibit formation of dental caries, (ii) reduce, repair or inhibit pre-carious lesions of the enamel, (iii) reduce or inhibit demineralization and promote remineralization of the teeth, (iv) reduce hypersensitivity of the teeth, (v) reduce or inhibit gingivitis, (vi) promote healing of sores or cuts in the oral cavity, (vii) reduce levels of acid producing bacteria, (viii) reduce or inhibit microbial biofilm formation in the oral cavity, (ix) reduce or inhibit plaque formation in the oral cavity, (x) promote systemic health, or (xi) clean teeth and oral cavity.

The invention further provides the use of a silica abrasive having a $N_2$ BET surface area of less than 50 $m^2/g$ and an Einlehner hardness of from 4 to 11 in a dentifrice composition comprising stannous fluoride to increase the stability of stannous and fluoride ions in the composition.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The invention provides, in a first embodiment, a dentifrice composition (Composition 1.0), for example an oral gel or toothpaste, that comprises stannous fluoride and a silica abrasive having a $N_2$ BET surface area of less than 50 $m^2/g$ and an Einlehner hardness of from 4 to 11.

For example, the invention includes:

1.1. Composition 1.0, wherein the silica abrasive has a $N_2$ BET surface area of from 1 $m^2/g$ to 50 $m^2/g$, e.g., from 1 $m^2/g$ to 45, from 1 $m^2/g$ to 40 $m^2/g$, from 1 $m^2/g$ to 35 $m^2/g$, or from 1 $m^2/g$ to 30 $m^2/g$ 1.2. Composition 1.0 or 1.1, wherein the silica abrasive has an average particle size of from 5 μm to 20 μm, e.g., from 8 μm to 13 μm, from 8 μm to 11 μm, or from 9 μm to 13 μm.

1.3 Any of the preceding compositions, wherein the silica abrasive has an oil absorption of from 60 cc/100 g to 120 cc/100 g, e.g., from 70 cc/100 g to 110 cc/100 g, or from 80 cc/100 g to 100 cc/100 g, e.g., linseed oil absorption.

1.4. Any of the preceding compositions, wherein the silica abrasive has an Einlehner hardness of from 5 to 10, or from 6 to 9.

1.5. Any of the preceding compositions, wherein Einlehner hardness is measured per 174,000 revolutions with a Brass screen.

1.6. Any one of compositions 1.0-1.4, wherein Einlehner hardness is measured per 100,000 revolutions with a brass screen.

1.7. Any of the preceding compositions having a pellicle cleaning ratio (PCR) of from 80 to 105, e.g., from 85 to 100, or from 90 to 95.

Any of the preceding compositions having a radioactive dentin abrasion (RDA) of less than 150, e.g., from 90 to 130, from 100 to 120, or from 105 to 115.

1.9. Any of the preceding compositions having a PCR/RDA ratio of from 0.5 to 1.5, e.g., from 0.7 to 1.3, from 0.8 to 1.2, about 0.8, or about 1.

1.10. Any of the preceding compositions, wherein the silica abrasive is from 1% to 95% by weight of the composition, e.g., from 5% to 30%, from 10% to 25%, from 10% to 20%, or from 15% to 25%.

1.11. Any of the preceding compositions, wherein the silica abrasive has a $d_{10}$ of from 2.5 µm to 2.9 µm.

1.12. Any of the preceding compositions, wherein the silica abrasive fragments when the oral composition is applied to a hard surface, e.g., enamel or dentin, in the oral cavity.

1.13. Any of the preceding compositions, wherein upon use of the composition in the oral cavity, the silica abrasive fragments into particles having a $d_{10}$ of from 2.3 µm to 2.6 µm.

1.14. Any of the preceding compositions, wherein the silica abrasive fragments when subjected to shear forces for sufficient amount of time.

1.15. Any of the preceding compositions, wherein the average particle size of the silica abrasive is reduced from 16% to 20% after being applied to a hard surface in the oral cavity.

1.16. Any of the preceding compositions, wherein the $d_{10}$ of the silica abrasive is reduced from 9% to 12% after being applied to a hard surface in the oral cavity.

1.17. Any of the preceding compositions, wherein the composition does not contain any silica abrasive having a $N_2$ BET surface area of greater than 50 $m^2/g$.

1.18. Any of the preceding compositions, wherein the composition does not contain any abrasive having a $N_2$ BET surface area of greater than 50 $m^2/g$.

1.19. Any of the preceding compositions wherein stannous fluoride is present in an amount of from 0.1% to 2% by weight, e.g., from 0.2% to 1% by weight, from 0.3% to 0.8 by weight, 0.4% to 0.7% by weight, from 0.5% to 0.6% or from 0.4% to 0.5% by weight, of the composition.

1.20. The composition of any preceding claim, wherein the composition further comprises other fluoride ion source which is not stannous fluoride.

1.21. The composition of any preceding claim, wherein the other fluoride ion source is selected from sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.

1.22. The composition of any preceding claim, wherein the composition further comprises other stannous ion source which is not stannous fluoride.

1.23. The composition of any preceding claim, wherein the other stannous ion source is selected from stannous chloride, stannous acetate and a combination thereof.

1.24. Any of the preceding compositions wherein the composition comprises a zinc ion source.

1.25. Any of the preceding compositions wherein the zinc ion source is selected from zinc citrate, zinc oxide and a combination thereof.

1.26. Any of the preceding compositions, wherein the composition comprises one or more thickeners, for example thickening silicas.

1.27. Any of the preceding compositions, wherein the composition comprises a foaming agent, for example a betaine, for example cocamidopropyl betaine.

1.28. Any of the preceding compositions, wherein the composition comprises ingredients selected from one or more of buffering agents, humectants, surfactants, gum strips or fragments, breath fresheners, flavoring, fragrance, coloring, antibacterial agents, whitening agents, agents that interfere with or prevents bacterial attachment, calcium sources, and potassium salts.

1.29. Any of the preceding compositions comprising water in an amount of 5% to 50%, e.g., 10% to 40%, or 20% to 30%, by weight of the composition.

1.30. Any of the preceding compositions effective upon application to the oral cavity, e.g., by brushing, to (i) reduce or inhibit formation of dental caries, (ii) reduce, repair or inhibit pre-carious lesions of the enamel, (iii) reduce or inhibit demineralization and promote remineralization of the teeth, (iv) reduce hypersensitivity of the teeth, (v) reduce or inhibit gingivitis, (vi) promote healing of sores or cuts in the oral cavity, (vii) reduce levels of acid producing bacteria, (viii) reduce or inhibit microbial biofilm formation in the oral cavity, (ix) reduce or inhibit plaque formation in the oral cavity, (x) promote systemic health, or (xi) clean teeth and oral cavity.

In another embodiment, the invention provides a method to (i) reduce or inhibit formation of dental caries, (ii) reduce, repair or inhibit pre-carious lesions of the enamel, (iii) reduce or inhibit demineralization and promote remineralization of the teeth, (iv) reduce hypersensitivity of the teeth, (v) reduce or inhibit gingivitis, (vi) promote healing of sores or cuts in the oral cavity, (vii) reduce levels of acid producing bacteria, (viii) reduce or inhibit microbial biofilm formation in the oral cavity, (ix) reduce or inhibit plaque formation in the oral cavity, (x) promote systemic health, or (xi) clean teeth and oral cavity, comprising applying an effective amount of any of dentifrice compositions as disclosed herein to the oral cavity of a subject in need thereof.

In another embodiment, the invention provides a method to improve oral health comprising applying an effective amount of any of dentifrice compositions as disclosed herein to the oral cavity of a subject in need thereof.

In another embodiment, the invention provides the use of any of dentifrice compositions as disclosed herein to (i) reduce or inhibit formation of dental caries, (ii) reduce, repair or inhibit pre-carious lesions of the enamel, (iii) reduce or inhibit demineralization and promote remineralization of the teeth, (iv) reduce hypersensitivity of the teeth, (v) reduce or inhibit gingivitis, (vi) promote healing of sores or cuts in the oral cavity, (vii) reduce levels of acid producing bacteria, (viii) reduce or inhibit microbial biofilm formation in the oral cavity, (ix) reduce or inhibit plaque formation in the oral cavity, (x) promote systemic health, or (xi) clean teeth and oral cavity, in a subject in need thereof.

In a further embodiment, the invention provides the use of a silica abrasive having a $N_2$ BET surface area of less than 50 $m^2/g$ and an Einlehner hardness of from 4 to 11 in a dentifrice composition comprising stannous fluoride to increase the stability of stannous and fluoride ions in the composition.

The silica abrasive of the present invention may have a $N_2$ BET surface area of less than 50 $m^2/g$. In some embodiments, the silica abrasive has a $N_2$ BET surface area of 1 to 45 $m^2/g$, to 40 $m^2/g$, or 1 to 30 $m^2/g$. In some embodiments, the dentifrice composition of the present invention does not contain any silica abrasive having a $N_2$ BET surface area of greater than 50 m/g. The $N_2$ BET surface area of silica abrasive may be determined using nitrogen as the adsorbent by the BET (Brunauer, Emmett and Teller) method. In this method, the surface area is calculated by fitting adsorption isotherms of nitrogen under specific conditions to a theoretically obtained adsorption model.

The silica abrasive of the present invention may have an average particle size of from 5 μm to 20 μm. In some embodiments, the silica abrasive has an average particle size of from 8 μm to 13 μm, from 8 μm to 11 μm, or from 9 μm to 13 m. Average particle size of particles may be measured by any means known in the art. For example, mean particle size may be measured using a Malvern Particle Size Analyzer, Model Mastersizer S, Malvern Instruments, Inc. (Southborough, Mass. USA), wherein a helium-neon gas laser beam is projected through a transparent cell that contains the abrasive suspended in an aqueous solution. Light rays that strike the particles are scattered through angles that are inversely proportional to the particle size. The photodetector array measures the quantity of light at several predetermined angles. Electrical signals proportional to the measured light flux values are then processed by a microcomputer system, against a scatter pattern predicted from theoretical particles as defined by the refractive indices of the sample and aqueous dispersant to determine the particle size distribution of the subject abrasive. The average particle size takes into account skewed particle sizes and the size distribution of the particles.

As used herein, $d_{10}$ refers to particles having a diameter that is 10% of the threshold of the sampled population (i.e., 10% of the population is equal to or smaller than the $d_{10}$ value). The silica abrasive of the present invention, when incorporated into an oral composition, breaks down or fractures as the oral composition is brushed against hard dental surfaces, e.g., dentin or enamel. The silica abrasive of the present invention, when incorporated into an oral composition, substantially retains their original size when the oral composition is brushed against soft surfaces of the oral cavity, or soft biofilms, e.g., pellicle or plaque.

The silica abrasive of the present invention may have an Einlehner hardness of from 4 to 11. In some embodiments, the silica abrasive has an Einlehner hardness of from 5 to 10, or from 6 to 9. Einlehner hardness may be determined by various means known by those of skill in the art. For example, an Einlehner At-1000 Abrader may measure the hardness of the abrasive particle in the following manner: a Fourdrinier metal screen, i.e., copper or brass, is weighed and exposed to the action of a suspension of the abrasive (for example, a 10% aqueous suspension of the abrasive) for a given number of revolutions. The hardness value is expressed as milligrams weight lost of the Fourdrinier wire screen per number of revolutions, e.g., 100,000 revolutions. In the present invention, Einlehner hardness of the silica abrasive utilized in the present invention is determined by utilizing a brass screen. 100 g of silica is added to 1L of water, and the slurry is rotated for 100,000 or 174,000 revolutions.

The silica abrasive of the present invention may have an oil absorption of from 60 cc/100 g to 120 cc/100 g linseed oil. In some embodiments, the silica abrasive has an oil absorption of from 70 cc/100 g to 110 cc/100 g, or from 80 cc/100 g to 100 cc/100 g. Oil absorption may be determined by various means known by those of skill in the art. For example, oil absorption may be determined by absorption of linseed oil or dibutyl phthalate (DBP) per 100 grams or abrasive. Oil absorption values can be measured using the ASTM Rub-Out Method D281.

PCR is a known method by those of skill in the art to measure the efficacy of removing tooth stains relative to a standard. The PCR method used herein is described in U.S. Pat. No. 5,658,553. In this method, a clear pellicle material is applied to a bovine tooth first, which is then stained with a combination of the pellicle material and tea, coffee and $FeCl_3$. The dentifrice compositions of the present invention may have a PCR of from 80 to 105. In some embodiments, the PCR is from 85 to 100, or from 90 to 95.

The dentifrice compositions of the present invention may have a RDA value of less than 150, e.g., from 90 to 130, from 100 to 120, or from 105 to 115. RDA values may be determined by any number of methods known by those of skill in the art. For example, RDA values may be determined according to the method set forth in U.S. Pat. No. 4,340,583. Generally, irradiated $^{32}P$ dentin is brushed, e.g., with an oral composition. The amount of dentin that is abraded away from the brushed dentin is quantified via analysis of $^{32}P$ which is observed in the abrasive slurry. The amount of dentin abrasion is referenced to a standard composition brushed on to the dentin, usually calcium pyrophosphate, which is set at an RDA value of 100. Generally, less abrasive compositions have lower RDA values.

The dentifrice compositions of the present invention may have a PCR/RDA ratio of from 0.5 to 1.5. In some embodiments, the PCR/RDA ratio may be 0.5, 0.6, 0.7, 0.8, 0.9, 1.0, 1.1, 1.2, 1.3, 1.4 or 1.5. The PCR/RDA ratio is used to determine the relative ratio of cleaning and abrasion characteristics of an oral care composition, e.g., a dentifrice or toothpaste composition.

Useful silica abrasive materials for preparing the oral compositions of the present invention may be obtained from Davison Chemical Division of W. R. Grace &. Co, (Baltimore, Md., USA) under the tradename Sylodent VP5, as described in United States Patent Application 2012/0100193 (the contents of which are incorporated herein by reference). The physical properties of Sylodent VP5 are shown in Table 1.

TABLE 1

|  | Sylodent VP5 |
|---|---|
| $N_2$ BET surface area ($m^2/g$) | <50 |
| Oil absorption (cc/100 g) | 80-100 |
| Mean particle size (μm) | 9-13 |
| d10 (μm) | 2.74 |
| Brass Einlehner hardness | 6-9 |

The use of Sylodent VP5 in oral care compositions imparts a superior cleaning ability, e.g., a high PCR value, and at the same time, reduces damage to hard dental surfaces, e.g., a low PDA, as shown in United States Patent Application 2012/0100193.

It has been found that the silica abrasive of the present invention exhibits high compatibility with stannous and fluoride ions. Without intending to be bound to theory, it is believed that surface area of the silica is an important characteristic in determining the extent to which stannous and fluoride ions are adsorbed onto the silica. It is believed that the silica abrasive of the invention provides less surface area to adsorb stannous and fluoride ions, therefore improving the compatibility with stannous and fluoride ions. At the same time, the silica of the present invention, when used in an oral care composition, provides a superior cleaning and/or polishing efficacy, while achieving a desirably low RDA that minimizes potential damage to enamel or dentin.

Thus, the silica abrasive of the invention is useful in oral care compositions containing stannous fluoride.

The dentifrice compositions of the present invention comprise a source of fluoride ion and a source of stannous ion. Preferably, the source of fluoride ions and the source of stannous ions is stannous fluoride. In some embodiments, stannous fluoride is present in an amount of from 0.1% to 2%, for example, from 0.2% to 1%, from 0.3% to 0.7%, 0.4% to 0.7%, from 0.5% to 0.6%, or from 0.4% to 0.5% by weight of the composition.

The dentifrice compositions of the present invention may contain other fluoride ion source which is not stannous fluoride. Fluoride ion sources are well known in the art and may be incorporated into the compositions of the present invention. Representative fluoride ion sources include, but are not limited to, sodium fluoride, potassium fluoride, sodium monofluorophosphate, sodium fluorosilicate, ammonium fluorosilicate, amine fluoride, ammonium fluoride, and combinations thereof. In some embodiments, the composition may contain fluoride ion sources in amounts sufficient to supply 25 ppm to 5,000 ppm of fluoride ions, generally at least 500 ppm, e.g., 500 to 2000 ppm, e.g., 1000 ppm to 1600 ppm, e.g., 1450 ppm. Fluoride ion sources may be added to the compositions of the invention at a level of 0.01% to 10%, e.g., 0.03% to 5%, or 0.1% to 1%, by weight of the composition. However, it is to be understood that the weights of fluoride salts to provide the appropriate level of fluoride ion will obviously vary based on the weight of the counter ion in the salt, and one of skill in the art may readily determine such amounts.

The dentifrice compositions of the present invention may contain other stannous ion source which is not stannous fluoride. Stannous ion sources are well known in the art and may be incorporated into the compositions of the present invention. In certain embodiments, the other stannous ion source is selected from stannous chloride, stannous acetate, and a combination thereof. In some embodiments, the dentifrice composition of the present invention may contain stannous ion sources in amounts sufficient to supply 3000 ppm to 15,000 ppm of stannous ions, e.g., 5,000 ppm to 13,000 ppm or from 7,000 ppm to 10,000 ppm. In some embodiments, stannous ion sources are present in the dentifrice composition in an amount of from 0.01% to 10%, e.g., from 0.5% to 7%, from 1% to 5%, from 1.5 to 4%, from 0.1% to 1%, from 0.2 to 0.5%, or from 0.3% to 0.4%, by weight of the composition. However, it is to be understood that the weights of stannous salts to provide the appropriate level of stannous ion will obviously vary based on the weight of the counter ion in the salt, and one of skill in the art may readily determine such amounts.

The dentifrice compositions of the present invention may include one or more zinc ion sources. Zinc ions have been found to help in the reduction of gingivitis, plaque, sensitivity, and improved breath benefits. The zinc ion source can be a soluble or sparingly soluble compound of zinc with inorganic or organic counter ions. Examples include zinc oxide, zinc sulfate, zinc chloride, zinc citrate, zinc lactate, zinc gluconate, zinc malate, zinc tartrate, zinc carbonate, zinc phosphate. In some embodiments, the zinc ion source is selected from zinc citrate, zinc oxide and a combination thereof. In some embodiments, the zinc ion source is present at a concentration of from 0.01% to 5%, e.g., 0.1% to 4%, or 1% to 3%, by weight of the composition.

The dentifrice compositions of the present invention may include other active ingredients. The active ingredients include, for example, anti-bacterial active agents, anti-tartar agents, anti-caries agents, anti-inflammatory agents, anti-sensitivity agents, basic amino acids, e.g., arginine, enzymes, nutrients, and the like. Actives useful herein are optionally present in the compositions of the present invention in safe and effective amounts that are sufficient to have the desired therapeutic or prophylactic effect in the human or lower animal subject to whom the active is administered, without undue adverse side effects (such as toxicity, irritation, or allergic response), commensurate with a reasonable risk/benefit ratio when used in the manner of this invention. The specific safe and effective amount of the active will vary with such factors as the particular condition being treated, the physical condition of the subject, the nature of concurrent therapy (if any), the specific active used, the specific dosage form, the carrier employed, and the desired dosage regimen.

The dentifrice compositions of the present invention may include one or more agents to increase the amount of foam that is produced when the oral cavity is brushed. Such foaming agents are known to those of skill in the art. Illustrative examples of agents that increase the amount of foam include, but are not limited to polyoxyethylene and certain polymers including, but not limited to, alginate polymers. The polyoxyethylene may increase the amount of foam and the thickness of the foam. Polyoxyethylene is also commonly known as polyethylene glycol ("PEG") or polyethylene oxide. The polyoxyethylenes suitable for this invention will have a molecular weight of 200,000 to 7,000,000, e.g., 600,000 to 2,000,000 or 800.000 to 1,000,000. The polyoxyethylene may be present in an amount of 1% to 90%, e.g., 5% to 50% or 10% to 20%, by weight of the the composition. The dosage of foaming agent in the composition (i.e., a single dose) is 0.01 to 0.9%, e.g., 0.05 to 0.5% or 0.1 to 0.2%, by weight of the composition.

The dentifrice compositions of the present invention may include at least one surfactant or solubilizer. Suitable surfactants include neutral surfactants (such as polyoxyethylene hydrogenated castor oil or fatty acids of sugars), anionic surfactants (such as sodium lauryl sulfate), cationic surfactants (such as the ammonium cation surfactants) or zwitterionic surfactants. These surfactants or solubilizers may be present in amounts of typically 0.01% to 2%; or from 1% to 2%; or about 1.5%, by weight of the composition.

The dentifrice compositions of the present invention may include a sweetener such as, for example, saccharin, for example sodium saccharin, acesulfam, neotame, cyclamate or sucralose; natural high-intensity sweeteners such as thaumatin, stevioside or glycyrrhizin; or such as sorbitol, xylitol, maltitol or mannitol. One or more of such sweeteners may be present in an amount of from 0.005% to 5% by weight, for example 0.01% to 1%, for example 0.01% to 0.5%, by weight of the composition.

The dentifrice compositions of the present invention may include one or more colorants. Colorants may include pigments, dyes, lakes and agents imparting a particular color or visual quality to the composition. Any orally acceptable colorant can be used. One or more colorants may optionally be present in the compositions in an amount of from 0.001% to 2%, for example from 0.001% to 0.01%, for example from 0.001% to 0.005% of the composition by weight.

The dentifrice compositions of the present invention may include one or more humectants. Humectants can reduce evaporation and also contribute towards preservation by lowering water activity, and can also impart desirable sweetness or flavor to compositions. Suitable humectants include edible polyhydric alcohols such as glycerin, sorbitol, xylitol, propylene glycol as well as other polyols and mixtures of these humectants. Other useful materials may also include orally acceptable alcohols, or polymers, e.g., such as polyvinylmethyl ether maleic acid copolymers, polysaccharides (e.g. cellulose derivatives, for example carboxymethyl cellulose, or polysaccharide gums, for example xanthan gum or carrageenan gum). In some embodiments, the humectant can be present in an amount of from 20% to 60%, for example from 30% to 50%, for example from 40% to 45%, by weight of the composition.

The dentifrice compositions of the present invention may include a preservative. Suitable preservatives include, for example, sodium benzoate, potassium sorbate, methylisothiazolinone, paraben preservatives, for example methyl p-hydroxybenzoate, propyl p-hydroxybenzoate, and mixtures thereof.

The dentifrice compositions of the present invention may include a flavoring agent. Suitable flavoring agents include, but are not limited to, essential oils and various flavoring aldehydes, esters, alcohols, and similar materials, as well as sweeteners such as sodium saccharin. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. The flavoring agent is typically incorporated in the oral composition at a concentration of 0.01 to 3% by weight.

The dentifrice compositions of the present invention may further comprise a pH adjuster. For example, the compositions may comprise an acid or base in an amount sufficient to adjust the pH of the compositions such that the compositions have a pH of from 4.0 to 9.0.

Water is present in the compositions of the present invention. Water employed in the preparation of commercial oral compositions should be deionized and free of organic impurities. Water commonly makes up the balance of the compositions and includes 5% to 50%, e.g., 10% to 40%, or 20% to 30%, by weight of the compositions. This amount of water includes the free water which is added plus that amount which is introduced with other materials or any components of the compositions described herein.

EXAMPLES

Example 1

The compatibility of several silica abrasives with stannous fluoride was determined as follows. A solution was prepared by adding 15% silica, 0.6% sodium gluconate and 0.454% stannous fluoride into water. The solution was stirred and left in a water bath for 15 days. After centrifugation at 10,000 RPM for 10 minutes, the supernatant was analyzed to measure the amounts of soluble tin, representing the available stannous ions, and soluble fluoride ions by standard methods. Measurements are presented in Table 2.

TABLE 2

| Silica Type | Soluble tin ppm | Soluble fluoride ppm |
|---|---|---|
| high cleaning silica (Zeodent 105) | 1800 | 621 |
| AC43 | 1400 | 884 |
| regular silica (Zeodent 114) | 2300 | 688 |
| low surface area silica (Sylodent VP5) | 2300 | 1015 |
| Prophy silica | 1000 | 995 |
| no silica | 3700 | 1188 |

The results show that although appreciable amounts of stannous and fluoride ions are adsorbed on the surface of all tested abrasives, low surface area silica exhibits the highest compatibility with both stannous and fluoride ions. The amounts of soluble stannous and fluoride ions in the presence of low surface silica are about 28% and 63% higher, respectively, compared to conventional high cleaning silica Zeodent 105.

Example 2

Dentifrice compositions were prepared having the formulations as indicated in Table 3.

TABLE 3

| Ingredient | Formula A | Formula B |
|---|---|---|
| Deionized water | 8.794 | 8.794 |
| Sweetening agents | 0.38 | 0.38 |
| Trisodium citrate | 3 | 3 |
| Citric acid | 0.6 | 0.6 |
| Stannous fluoride | 0.454 | 0.454 |
| Zinc citrate trihydrate | 0.5 | 0.5 |
| Zinc oxide | 1 | 1 |
| Polyphosphates | 3 | 3 |
| Humectants | 48.562 | 48.562 |
| Thickening agents | 2.85 | 2.85 |
| Dye | 0.004 | 0.004 |
| Low surface area silica (Sylodent VP5) | 24 | 0 |
| Regular silica | 0 | 12 |
| High cleaning silica | 0 | 7 |
| AC43 silica | 0 | 5 |
| Surfactants | 2.75 | 2.75 |
| Flavor | 1.8 | 1.8 |
| Synthetic anionic polymers | 0.606 | 0.606 |
| Titanium dioxide | 0.15 | 0.15 |
| 85% phosphoric acid | 0.55 | 0.55 |
| Sodium phosphate | 1 | 1 |
| Total | 100 | 100 |

Each of the formulations contains 0.454% stannous fluoride, 0.5% zinc citrate and 1% zinc oxide. Formulations A and B are different in that Formulation A contains 24% low surface area silica, whereas Formulation B contains 12% regular silica, 7% high cleaning silica and 5% AC 43 silica. The formulations were prepared initially as a premix by dissolving the stannous fluoride in an aqueous solution of citric acid and sodium citrate. The citrate ions in the premix chelate the stannous ion thereby preventing or inhibiting precipitate of the stannous salt in the final composition and reducing the chance of forming insoluble inactive tin compounds in the dentifrice composition. The premix was then mixed with the remaining active constituents and the vehicle of the dentifrice composition. The dentifrice compositions were subjected to an aging study to determine the compatibility of low surface area silica and a high cleaning silica system (12/7/5) consisting of 12% regular silica, 7% high cleaning silica and 5% AC43 with stannous, fluoride, and zinc ions in the dentifrice composition. The amounts of soluble fluoride, soluble tin, and soluble zinc ions were measured at initial, 4, 8, and 13 weeks by standard methods. Measurements are presented in Table 4.

TABLE 4

|  |  | Initial | 4 weeks | 8 weeks | 13 weeks |
|---|---|---|---|---|---|
| 24% low surface area silica | soluble fluoride | 1139 ppm | 1096 ppm | 1126 ppm | 1009 ppm |
|  | soluble tin | 0.31 wt. % | 0.30 wt. % | 0.28 wt. % | 0.30 wt. % |
|  | soluble zinc | 0.65 wt. % | 0.65 wt. % | 0.63 wt. % | 0.66 wt. % |
| 12% Regular/ 7% HCS/5% AC43 | soluble fluoride | 993 ppm | 1034 ppm | 1010 ppm | 902 ppm |
|  | soluble tin | 0.26 wt. % | 0.26 wt. % | 0.25 wt. % | 0.24 wt. % |
|  | soluble zinc | 0.63 wt. % | 0.65 wt. % | 0.61 wt. % | 0.64 wt. % |

The amounts of soluble fluoride and stannous ions in formulation A containing low surface area silica are higher, compared to formulation B containing the 12/7/5 high cleaning silica system, at initial, 4, 8, and 13 weeks, while there is no significant difference in the amount of soluble zinc between formulations A and B at initial, 4, 8, and 13 weeks. The results show that less amounts of stannous and fluoride ions are adsorbed on the surface of low surface area silica initially, compared to the 12/7/5 high cleaning silica system. The results further show that the stability of stannous and fluoride ions remains higher in the presence of low surface area silica over a long period of time, compared to the 12/7/5 high cleaning silica system. These results suggest that low surface area silica can be used as an abrasive in a dentifrice composition comprising stannous fluoride to provide high compatibility with fluoride and stannous ions.

Example 3

$N_2$ BET surface area of low surface area silica (Sylodent VP5), Zeodent 105 (high cleaning silica) and Zeodent 114 (regular silica) was determined. Measurements are presented in Table 5.

TABLE 5

|  | Low surface area silica | Zeodent 105 | Zeodent 114 |
|---|---|---|---|
| $N_2$ BET surface area (m$^2$/g) | <50 | 350-450 | 70-100 |

The $N_2$ BET surface area analysis shows that low surface area silica (Sylodent VP5) has a reduced surface area, compared to conventional high cleaning silica Zeodent 105 and regular silica Zeodent 114.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the scope of the invention should be construed broadly as set forth in the appended claims.

What is claimed is:

1. A dentifrice composition comprising:
   a zinc ion source present in an amount of 1 wt. % to 3 wt. %, based on the total weight of the composition, wherein the zinc ion source comprises the combination of zinc oxide and zinc citrate;
   stannous fluoride; and
   a silica abrasive having a $N_2$ BET surface area of less than 50 m$^2$/g, an Einlehner hardness of from 4 to 11, and an oil absorption of from 80 cc/100 g to 100 cc/100 g.

2. The composition of claim 1, wherein the silica abrasive has an average particle size of from 5 μm to 20 μm.

3. The composition of claim 1, wherein the silica abrasive has a silica abrasive having a $N_2$ BET surface area of from 1 to 50 m$^2$/g, an Einlehner hardness of from 6 to 9, an average particle size of 9 μm to 13 μm, and an oil absorption of from 80 cc/100 g to 100 cc/100 g.

4. The composition of claim 1 having a pellicle cleaning ratio of from 80 to 105.

5. The composition of claim 1 having a radioactive dentin abrasion of less than 150.

6. The composition of claim 1 having a PCR/RDA ratio of from 0.5 to 1.5.

7. The composition of claim 1, wherein the silica abrasive is present in an amount of from 1% to 95% by weight of the composition.

8. The dentifrice composition of claim 1, wherein the dentifrice composition does not comprise any silica abrasive having a $N_2$ BET surface area of greater than 50 m$^2$/g.

9. The composition of claim 1, wherein stannous fluoride is present in an amount of from 0.1% to 2% by weight of the composition.

10. The composition of claim 1, wherein the composition further comprises other fluoride ion source which is not stannous fluoride.

11. The composition of claim 1, wherein the composition further comprises other stannous ion source which is not stannous fluoride.

12. The composition of claim 1, wherein the composition comprises ingredients selected from one or more of buffering agents, humectants, surfactants, gum strips or fragments, breath fresheners, flavoring, fragrance, coloring, antibacterial agents, whitening agents, agents that interfere with or prevents bacterial attachment, calcium sources, and potassium salts.

13. The composition of claim 1 for use to (i) reduce or inhibit formation of dental caries, (ii) reduce, repair or inhibit pre-carious lesions of the enamel, (iii) reduce or inhibit demineralization and promote remineralization of the teeth, (iv) reduce hypersensitivity of the teeth, (v) reduce or inhibit gingivitis, (vi) promote healing of sores or cuts in the oral cavity, (vii) reduce levels of acid producing bacteria, (viii) reduce or inhibit microbial biofilm formation in the oral cavity, (ix) reduce or inhibit plaque formation in the oral cavity, (x) promote systemic health, or (xi) clean teeth and oral cavity.

14. A method of (i) reducing or inhibiting formation of dental caries, (ii) reducing, repairing or inhibiting pre-carious lesions of the enamel, (iii) reducing or inhibiting demineralization and promoting remineralization of the teeth, (iv) reducing hypersensitivity of the teeth, (v) reducing or inhibiting gingivitis, (vi) promoting healing of sores or cuts in the oral cavity, (vii) reducing levels of acid producing bacteria, (viii) reducing or inhibiting microbial biofilm formation in the oral cavity, (ix) reducing or inhibiting plaque formation in the oral cavity, (x) promoting systemic health, or (xi) cleaning teeth and oral cavity, comprising applying a dentifrice according to claim 1 to the teeth.

\* \* \* \* \*